(12) United States Patent
Chaudot et al.

(10) Patent No.: US 10,413,341 B2
(45) Date of Patent: Sep. 17, 2019

(54) BONE-FIXATION PLATE FOR THE DISTAL FIBULA AND DEVICE FOR DISTAL TIBIOFIBULAR SYNDESMOSIS FIXATION

(71) Applicant: ARTHREX, INC., Naples, FL (US)

(72) Inventors: Audrey Chaudot, München (DE); Gerlinde Michel, München (DE)

(73) Assignee: ARTHREX, INC., Naples, FL (US)

( * ) Notice: Subject to any disclaimer, the term of this patent is extended or adjusted under 35 U.S.C. 154(b) by 358 days.

(21) Appl. No.: 15/372,724

(22) Filed: Dec. 8, 2016

(65) Prior Publication Data
US 2017/0156767 A1    Jun. 8, 2017

(30) Foreign Application Priority Data
Dec. 8, 2015 (EP) ...................................... 15198425

(51) Int. Cl.
*A61B 17/80* (2006.01)
(52) U.S. Cl.
CPC .......... *A61B 17/8061* (2013.01); *A61B 17/80* (2013.01); *A61B 17/8057* (2013.01)
(58) Field of Classification Search
CPC . A61B 17/80; A61B 17/8052; A61B 17/8057; A61B 17/8061
See application file for complete search history.

(56) References Cited

U.S. PATENT DOCUMENTS

| | | | | |
|---|---|---|---|---|
| 5,190,545 A * | 3/1993 | Corsi | ..................... | A61B 17/82 606/309 |
| 6,338,734 B1 * | 1/2002 | Burke | ..................... | A61B 17/74 606/280 |
| 8,118,848 B2 * | 2/2012 | Ducharme | ......... | A61B 17/8061 606/280 |
| 8,343,155 B2 * | 1/2013 | Fisher | ..................... | A61B 17/80 606/74 |
| 8,425,574 B2 * | 4/2013 | Huebner | ............ | A61B 17/1728 606/281 |
| 8,496,665 B2 * | 7/2013 | Cavallazzi | ......... | A61B 17/1728 408/202 |
| 9,179,950 B2 * | 11/2015 | Zajac | ................. | A61B 17/0401 |
| 9,259,217 B2 * | 2/2016 | Fritzinger | .......... | A61B 17/0401 |
| 9,549,768 B2 * | 1/2017 | Finley | ................ | A61B 17/8004 |
| 2004/0087954 A1 * | 5/2004 | Allen | ..................... | A61B 17/82 606/74 |
| 2006/0173458 A1 * | 8/2006 | Forstein | ............. | A61B 17/1728 606/86 B |
| 2007/0233111 A1 * | 10/2007 | Orbay | ................ | A61B 17/1728 606/286 |
| 2008/0051786 A1 * | 2/2008 | Jensen | ............... | A61B 17/8057 606/86 A |
| 2009/0204121 A1 * | 8/2009 | Cavallazzi | ......... | A61B 17/1728 606/96 |
| 2009/0281543 A1 * | 11/2009 | Orbay | .................... | A61B 17/80 606/70 |

(Continued)

OTHER PUBLICATIONS

Extended European Search Report for Application No. EP 16 20 2941 dated May 10, 2017.

*Primary Examiner* — Eric S Gibson
(74) *Attorney, Agent, or Firm* — Carlson, Gaskey & Olds (57) ABSTRACT

This disclosure relates to bone fixation plate and a system for treatment of injuries of the distal tibiofibular syndesmosis. The bone fixation plate provides an improved stability to the distal fibula.

19 Claims, 9 Drawing Sheets

(56) References Cited

U.S. PATENT DOCUMENTS

| | | | |
|---|---|---|---|
| 2009/0287215 A1* | 11/2009 | Fisher | A61B 17/80 606/71 |
| 2009/0312758 A1* | 12/2009 | Petit | A61B 17/74 606/60 |
| 2009/0312759 A1* | 12/2009 | Ducharme | A61B 17/8061 606/70 |
| 2010/0234896 A1* | 9/2010 | Lorenz | A61B 17/74 606/286 |
| 2012/0083848 A1* | 4/2012 | Gonzalez-Hernandez | A61B 17/0401 606/281 |
| 2012/0123474 A1* | 5/2012 | Zajac | A61B 17/0401 606/232 |
| 2013/0123841 A1* | 5/2013 | Lyon | A61B 17/0401 606/232 |
| 2014/0107798 A1* | 4/2014 | Jeng | A61F 2/4202 623/21.18 |
| 2014/0155944 A1* | 6/2014 | Truman | A61B 17/0401 606/324 |
| 2014/0243907 A1* | 8/2014 | Cavallazzi | A61B 17/74 606/286 |
| 2014/0277177 A1* | 9/2014 | Gonzalez-Hernandez | A61B 17/8057 606/281 |
| 2014/0277178 A1* | 9/2014 | O'Kane | A61B 17/8061 606/286 |
| 2014/0336712 A1 | 11/2014 | Strnad et al. | |
| 2015/0051601 A1 | 2/2015 | Larsen et al. | |
| 2015/0066093 A1* | 3/2015 | Lin | A61B 17/8057 606/291 |
| 2015/0297271 A1* | 10/2015 | Finley | A61B 17/8004 606/281 |
| 2015/0327899 A1* | 11/2015 | Early | A61B 17/80 606/280 |
| 2016/0166297 A1* | 6/2016 | Mighell | A61B 17/8057 606/291 |
| 2016/0166298 A1* | 6/2016 | Mighell | A61B 17/8061 606/280 |
| 2016/0262814 A1* | 9/2016 | Wainscott | A61B 17/8061 |
| 2017/0156767 A1* | 6/2017 | Chaudot | A61B 17/80 |
| 2017/0209194 A1* | 7/2017 | Ricker | A61B 17/8061 |
| 2017/0252080 A1* | 9/2017 | Steinhauer | A61B 17/8061 |
| 2018/0153601 A1* | 6/2018 | Riley | A61F 2/08 |
| 2018/0318097 A1* | 11/2018 | Armacost | A61F 2/4225 |

* cited by examiner

BONE-FIXATION PLATE FOR THE DISTAL FIBULA AND DEVICE FOR DISTAL TIBIOFIBULAR SYNDESMOSIS FIXATION

CROSS-REFERENCE TO RELATED APPLICATIONS

This application claims priority to pending European Application No. 15 198 425.9, which was filed on Dec. 8, 2015.

BACKGROUND

1. Technical Field

This disclosure relates to ankle surgery and, more particularly, to a bone fixation plate, and a device for distal tibiofibular syndesmosis fixation.

Ankle injuries are among the most common of the bone and joint injuries. The ankle joint is formed of three bones coming together: the tibia which makes up the medial, or inside, anklebone; the fibula which parallels the tibia and makes up the lateral, or outside, anklebone; and the talus. The far ends of the tibia and fibula are known as the malleoli and together they form an arch that sits on top of the talus.

A fibrous membrane (the joint capsule) encases the joint architecture and is lined with a smoother layer called the synovium. The joint capsule contains the synovial fluid produced by the synovium. The synovial fluid allows for smooth movement of the joint surfaces. The ankle joint is stabilized by three groups of ligaments, which are fibers that hold these bones in place.

Surgery to repair an ankle fracture is indicated for patients who suffer a displaced ankle fracture involving the bone on the inside of the ankle (tibia), the bone on the outside of the ankle (fibula), or both. As the fibula is much narrower than the tibia at the ankle joint, a fracture of the fibula is much more frequent than a fracture of the tibia. One injury that may occur in the ankle is a disruption of the distal tibiofibular syndesmosis. A syndesmotic injury is a disruption of the strong fibrous ligaments that hold the fibula and tibia together near the ankle joint. If the syndesmosis is disrupted, then the ankle joint will be unstable and surgery is usually indicated.

The distal tibiofibular syndesmosis is usually described as being comprised of four ligaments. These ligaments are the anterior inferior tibiofibular ligament (AITFL), the posterior inferior tibiofibular ligament (PITFL), the transverse ligament (TL), and the interosseous ligament (IL). The primary role of these ligaments is to act as tensile members that stabilize the fibula within the distal tibiofibular joint. Injury to these ligaments, either isolated or concomitant with fractures of one or both the tibia and fibula, results in diastasis of the ankle joint which manifests as ankle instability.

As used herein, the term "syndesmosis" is intended to mean an articulation of bones, in particular those portions of the tibia and fibula forming the ankle, in which the bones are joined by means of a ligament. Thereby, the distal tibiofibular syndesmosis is a syndesmotic joint formed by two bones and four ligaments. The distal tibia and fibula form the osseous part of the syndesmosis and are linked by the above mentioned anterior inferior tibiofibular ligament (AITFL), the posterior inferior tibiofibular ligament (PITFL), the transverse ligament (TL), and the interosseous ligament (IL). Although the syndesmosis is a joint, in the literature the term syndesmotic injury is used to describe injury of the syndesmotic ligaments. Sometimes the transverse ligament (TL) is also called inferior transverse ligament of the tibiofibular syndesmosis. As the transverse ligament (TL) lies in front of the posterior inferior tibiofibular ligament (PITFL) and is very close to the latter, for purposes of reconstruction, these two ligaments can be regarded as a single ligament. Therefore, although there are four ligaments in the distal tibiofibular syndesmosis, if this disclosure mentions three ligaments of the distal tibiofibular syndesmosis, it is understood that the transverse ligament (TL) and the posterior inferior tibiofibular ligament (PITFL) are counted as a single ligament.

2. Description of Relevant Art

US 2015/0051601 A1 relates to an apparatus and method for syndesmosis fixation. It shows an assembly including two pieces. The first piece is an oblong bone plate and the second piece is a small bone plate placed on top of the bone plate. Three sutures are fixed on the one end at the small bone plate and on the other end in the tibia, with one suture penetrating the fibula.

SUMMARY

The embodiments are based on the object of providing a bone fixation plate giving improved stability to the distal fibula and a device for distal tibiofibular syndesmosis fixation.

A further object is to provide a single device which is configured to treat most kinds of distal tibiofibular syndesmosis injuries, i.e. fractures of the distal fibula and injuries of the anterior inferior tibiofibular ligament (AITFL), the posterior inferior tibiofibular ligament (PITFL), and the transverse ligament (TL), in a better and easier way than devices of the prior art. The device should be able to reconstruct the function of the natural ligaments, i.e. the reconstructed ligaments should be at nearly the same place as the natural ligaments and have a similar functionality. Further, the reconstructed ligaments should be flexible, resilient, but also resistive, durable and robust.

In an embodiment, a bone fixation plate is configured for treatment of fractures of the distal fibula, including fractures of the distal fibula which occur together with injuries of the four ligaments of the distal tibiofibular syndesmosis, i.e. the anterior inferior tibiofibular ligament (AITFL), the posterior inferior tibiofibular ligament (PITFL), the transverse ligament (TL), and the interosseous ligament (IL).

A bone fixation plate includes an elongate body which is adapted to be placed on the distal fibula. The elongate body has a proximal end, a distal end, an inner surface, and an outer surface. An elongate body of the bone fixation plate may further comprise at least one lateral edge, in particular a single circumferential edge, which is arranged between the inner surface and the outer surface of the bone fixation plate. The elongate body of the bone fixation plate may comprise a single edge, which may be circumferential.

The elongate body of the bone fixation plate may comprise four edges, i.e. a superior or upper edge, an inferior or lower edge, an anterior edge, and a posterior edge.

The elongate body further includes at least one hole which is adapted for a screw to be fixed therein and/or a flexible strand, or construct thereof, to be guided through the hole. An end of the flexible strand may be guided through the at least one hole of the elongate body and may be fixed at a button which rests at the at least one hole on the outer surface of the elongate body. The at least one hole can be configured to attach the bone fixation plate to the distal fibula. This is can be achieved using a plurality of screws. A screw configured for the at least one hole may be a locking or a non-locking screw.

A flexible strand can be a suture, a tape, etc. A flexible strand construct can be a flexible strand (e.g., suture, tape, etc.) in combination with a fixation device, such as a button or an anchor.

An elongate body may further comprise at least one wing which is connected with the elongate body and which extends from a lateral edge of the elongate body.

The at least one wing can be a part of the elongate body.

The at least one wing may comprise at least one hole for fixing a flexible strand to the bone fixation plate. Each wing may comprise a single hole for fixing a flexible strand to the bone fixation plate. The flexible strand may be fixed to the bone fixation plate by fixing the flexible strand to a button which rests at the at least one hole on the surface of the at least one wing.

The at least one wing may extend from the lateral edge of the elongate body in a direction which can be orthogonal to the longitudinal axis of the elongate body. It may also extend under an angle either towards the proximal or distal end of the bone fixation plate.

The direction under which the at least one wing extends from the lateral edge of the elongate body may have an angle between 20° and 70° with respect to the plane of the elongate body.

The elongate body may be adapted to be placed on the distal fibula, the proximal end is adapted to face an upper part of the distal fibula, the distal end is adapted to face a distal end the distal fibula, the inner surface is adapted to face the lateral surface of the distal fibula, the outer surface is adapted to face away from the lateral surface of the distal fibula, and the at least one wing is adapted to extend from a lateral edge or a part of the lateral circumferential edge of the elongate body towards the anterior surface and/or the posterior surface of the distal fibula.

When the bone fixation plate is used as intended, i.e. when the bone fixation plate is fixed onto the distal fibula, in particular to the lateral surface of the distal fibula, the proximal end of the bone fixation plate points towards the proximal end of the fibula or the knee, and the distal end of the bone fixation plate points towards the distal end of the fibula or towards the ankle.

The term "used as intended" may, for example, mean that the relevant object is located at the position and/or is arranged in the orientation at/in which it should be used. For example, a bone fixation plate is located on top of the distal fibula.

A bone fixation plate can comprise two wings, e.g., a first wing and a second wing. A first wing and second wing can be arranged on opposite sides at the lateral edge of the elongate body.

Two wings can be arranged symmetrically with respect to a plane which is orthogonal to the outer surface or the elongate body and parallel to the longitudinal axis of the elongate body, wherein the longitudinal axis of the elongate body lies within the plane. This plane may also be described as the plane which goes through the longitudinal axis of the elongate body and is orthogonal to the outer surface of the elongate body. In an alternate embodiment, the wings can be arranged asymmetrically either in length, angulation towards inferior/posterior or angulation towards medial/lateral.

A first wing and a second wing can be adapted to be arranged symmetrically with respect to a coronal plane through the distal fibula or a plane along the longitudinal axis of the elongate body which is orthogonal to the outer surface of the elongate body. When referring to a different location with respect to a superior-inferior direction, this disclosure refers to different level or height.

A first wing can comprise a first hole which is adapted for a first flexible strand to be guided through the hole, and a second wing can comprise a second hole which is adapted for a second flexible strand to be guided through the hole. The first flexible strand can be fixed to a button which can rest on the first hole of the first wing. The second flexible strand can be fixed to a button which can rest on the second hole of the second wing.

Each wing can comprise at least one hole which is adapted for a flexible strand to be guided through the hole. The flexible strand can be fixed to the bone fixation plate by fixing the flexible strand to a button which can rest on the at least one hole. Each wing can comprise a single hole which is adapted for a flexible strand to be guided through the hole. The flexible strand can be fixed to the bone fixation plate by fixing the flexible strand to a button which rests on the single hole of each wing.

A first wing can be adapted to extend towards the anterior surface of the distal fibula, and the second wing can be adapted to extend towards the posterior surface of the distal fibula.

In an embodiment, the bone fixation plate does not extend up to the anterior or posterior surface or border of the distal fibula. Thereby, the bone fixation plate does not interfere, in particular contact or touch, with the distal tibia, even when the ankle or foot is distorted.

The bone fixation plate can extend from a middle vertical axis of the lateral surface of the fibula to a point on the distal fibula which has an angle of about 40° to about 90° with respect to the center of the distal fibula. This angle can be about 80°, about 70°, about 60°, about 55°, about 50°, about 45°, or about 40°.

The at least one wing, e.g., a first wing and/or a second wing, can be arranged at approximately the same height as the fibular notch of the tibia or at approximately the same height as the tibiofibular joint.

The at least one wing, e.g., a first wing and/or a second wing, can be arranged at approximately the same height as the insertion points of the anterior inferior tibiofibular ligament or the posterior inferior tibiofibular ligament. The first wing can be arranged at approximately the same height as the anterior inferior tibiofibular ligament. The second wing can be arranged at approximately the same height as the posterior inferior tibiofibular ligament.

The at least one wing can be arranged at approximately the same height as the Chaput tubercle of the tibia or at the same height as the Volksmann's tubercle of the tibia.

In an embodiment, the first wing is arranged at the same height as the Chaput tubercle of the tibia, and the second wing is arranged at the same height as the Volksmann's tubercle of the tibia.

The center of each wing can be arranged at a level in the middle between the proximal and the distal end, wherein "the middle" is at a point about 30% to about 70%, about 40% to about 60%, about 45% to about 60%, about 50% to about 60%, about 40% to about 55%, about 40% to about 50%, about 45% to about 50%, or about 45% to about 55% of the total length of the elongate body from the distal end. In an embodiment, the middle can be a point about 30%, about 40%, about 45%, about 50%, about 55%, about 60%, about 65%, or about 70% of the total length of the elongate body from the distal end.

Each wing can also be arranged in the inferior third, fourth, or fifth of the elongate body.

Each wing can be arranged about 10 to 20% of the total length of the elongate body below the middle of the elongate body.

The bone fixation plate can comprise titanium, stainless steel, PEEK or any other surgically acceptable material having a mechanical strength sufficient for a bone fixation plate.

The device for distal tibiofibular syndesmosis fixation is intended to treat fractures of the distal fibula using the bone fixation plate and to assist repair the function of the ligaments of a natural distal tibiofibular syndesmosis using flexible strands.

A device for distal tibiofibular syndesmosis fixation includes a bone fixation plate and at least one flexible strand. The at least one flexible strand has a first end and a second end, wherein the first end of the at least one flexible strand is adapted to be guided through the at least one hole of the bone fixation plate and the second end of the at least one flexible strand is adapted to be fixed on the medial surface of the tibia. The first end of the at least one flexible strand can be fixed to a button which can rest on the at least one hole of the bone fixation plate. The second end of the at least one flexible strand can be fixed to a button which rests on the medial surface of the tibia. Here, the at least one flexible strand is adapted to be arranged in a hole through the tibia bone and/or the distal fibula.

The following may apply to each flexible strand of the present disclosure. Each end of each flexible strand, which is fixed or attached to or at the bone fixation plate, may be fixed to the bone fixation plate using a button or an anchor. This can be done by fixing an end of the flexible strand to the button which rests on at a hole on the surface of the bone fixation plate. The end of the flexible strand can be guided through a hole extending through the bone fixation plate and the end of the flexible strand can be fixed to the button.

The following may apply to each flexible strand of the present disclosure. Each end of each flexible strand which is fixed on a surface of a bone may be fixed there by fixing an end of the flexible strand to a button which rests on the surface of the bone. This may be done by guiding the end of the flexible strand through a hole extending to the surface of the bone and by fixing the end of the flexible strand to the button.

Each flexible strand which according to this disclosure is adapted to be fixed with its first end to the bone fixation plate and with its second end to the medial surface of the tibia may e.g. be a suture or a suture-button construct, e.g. a TightRope®.

According to another embodiment, the device includes three flexible strands, i.e. a first flexible strand (e.g., a first suture or construct thereof), a second flexible strand (e.g., a second suture or construct thereof), and a third flexible strand (e.g., a third suture or construct thereof), wherein each flexible strand (e.g., suture or construct thereof) has a first and a second end, and the bone fixation plate includes two wings, i.e. the first wing and the second wing. Here, each flexible strand is used to repair one ligament of the three ligaments of the distal tibiofibular syndesmosis, wherein the transverse ligament (TL) and the posterior inferior tibiofibular ligament (PITFL) are counted as a single ligament.

The first wing and the second wing can be arranged on opposite sides on the lateral edge of the elongate body. In an embodiment, the first wing and the second wing are symmetrical with respect to a coronal plane through the distal fibula or a plane along the axis of the elongate body which is orthogonal to the outer surface of the elongate body. In an embodiment, the first wing and the second wing are asymmetrical with respect to a coronal plane through the distal fibula or a plane along the axis of the elongate body which is orthogonal to the outer surface of the elongate body.

The first wing is adapted to extend towards the anterior surface of the distal fibula and the second wing is adapted to extend towards the posterior surface of distal fibula. However, the wings should not interfere with the lateral surface of the tibia or any other anatomical part which might hinder movement of the patient.

Each wing may directly contact the lateral surface of the fibula, however, the hole of each wing should not fully contact the lateral surface of the fibula. A gap between the wing at the position of the hole and the fibula allows a flexible strand to pass through the hole in the wing and along the fibula at the outside of the fibula. The flexible strand(s) may be fixed at the wing using a button, an anchor, or a button and anchor. To adapt the wings to a specific anatomy, at least one wing can be malleable to bend the at least one wing. Furthermore, at least one wing may be cut if needed.

Each wing includes at least one hole for fixing a flexible strand. In an embodiment, each wing has a single hole.

The first end of the first flexible strand can be adapted to be fixed at the first hole of the first wing, and the second end of the first flexible strand can be adapted to be fixed at the medial surface of the tibia, wherein the first flexible strand is adapted to extend through a first hole in the tibia extending from an anterior position on the lateral surface of the tibia to a position (e.g., anterior) on the medial surface of the tibia. Both ends of the first flexible strand may be fixed using buttons.

The first end of a second flexible strand can be adapted to be fixed at the second hole of the second wing, and the second end of the second flexible strand can be adapted to be fixed at the medial surface of the tibia. A third flexible strand can be adapted to extend through a third hole in the tibia extending from a posterior position on the lateral surface of the tibia to a position (e.g., a posterior position) on the medial surface of the tibia.

The first end of the third flexible strand can be adapted to be fixed at the at least one hole in the elongate body, and the second end of the third flexible strand is adapted to be fixed at the medial surface of the tibia. The third flexible strand can be adapted to extend through a hole in the fibula and a hole in the tibia. The hole in the fibula is adapted to extend from the lateral surface to the medial surface of the fibula, and the hole in the tibia is adapted to extend from the lateral surface to the medial surface of the tibia, wherein the hole in the fibula is aligned with the hole in the tibia. This alignment need not be perfect. When a flexible strand (e.g., suture, tape, etc.) can go through the two holes without being harmed is sufficient.

The position where a first flexible strand is adapted to be fixed on the medial surface of the tibia can be anterior as compared to the position where a second flexible strand is adapted to be fixed on the medial surface of the tibia.

A first hole through the tibia, through which the first flexible strand is adapted to run, can be arranged at the level of the tibiofibular joint. A second hole through the tibia, through which the second flexible strand is adapted to run, can be arranged at the level of the tibiofibular joint. The first hole and the second hole can be arranged at the same height or level. The two wings and the two holes through the tibia can be arranged at the same level, which can be at the level of the tibiofibular joint.

The hole for the third flexible strand, which can be adapted to be arranged in the fibula and in the tibia can be arranged above the level of the tibiofibular joint, or even at the level of the interosseous ligament or at a level slightly above the upper end of the distal tibiofibular joint articular cartilage.

Any flexible strand can be adapted to be arranged transversally or in a transverse plane.

The position where the first flexible strand is adapted to be fixed on the medial surface of the tibia can be at approximately the same height as the position where the second flexible strand is adapted to be fixed on the medial surface of the tibia.

The first end or the second end of the at least one flexible strand or the first end or the second end of the first, second, or third flexible strand can be adapted to be fixed at the tibia, the at least one hole of the bone fixation plate, the first hole of the first wing or the second hole of the second wing using a button.

In an embodiment, the first flexible strand and second flexible strand are not parallel to each other. When viewed in a transverse plane and from the medial surface of the tibia, the first and second flexible strands are adapted to be divergent towards the lateral surface of the tibia, which increases rotational stability of the syndesmosis.

The first flexible strand, the second flexible strand, and the third flexible strand each can be adapted to lie approximately within a transverse plane. For example, the first flexible strand and the second flexible strand can be adapted to lie approximately within the same transverse plane, while the second flexible strand is adapted to lie in a different transverse plane.

The first flexible strand, the second flexible strand, and the third flexible strand can be adapted such that projections of the first flexible strand, the second flexible strand, and the third flexible strand into a transverse plane are divergent when viewed from the medial surface of the tibia. In an embodiment, the projection of the third flexible strand is arranged between the projections of the first flexible strand and the second flexible strand. These features can have the advantage of increasing rotational stability of the syndesmosis.

In an embodiment, a device for distal tibiofibular syndesmosis fixation may be installed as follows. In a first step, a bone fixation plate is fixed on the lateral surface of the distal fibula. Fixation can be achieved by screwing a bone fixation plate to the distal fibula using holes in the elongate body. The holes can be arranged to achieve a good healing effect for the fibula.

Further holes in the bone fixation plate are present for fixing flexible strands to the plate which are installed in subsequent steps. Three flexible strands are utilized for the anterior inferior tibiofibular ligament (AITFL), the posterior inferior tibiofibular ligament (PITFL), and the interosseous ligament (IL In an embodiment, each flexible strand is a suture.

The order in which the three flexible strands are fixed to the tibia and the fibula does not matter. In an embodiment, the third flexible strand is fixed first because the drilling or hole through the tibia is at a right angle with respect to the lateral surfaces of the tibia and fibula. Also, the tibia and the fibula can be fixed to each other by installing the third flexible strand, and as a consequence the tibia and fibula then are in the place where they should be after the surgery and no repositioning of these bones is necessary.

The third flexible strand can include a first button, which can be oblong and can rest on the medial surface of the tibia, and a second button, which can be round and can rest on the outer surface of the elongate body of the bone fixation plate which itself is on the lateral surface of the fibula. The third flexible strand can also include a flexible member or thread, which is arranged between the first and the second button and which has two free ends emerging from the second button at its rear end. For installation of the third flexible strand, pull-through flexible strands can be used, which are then removed after installation.

The third flexible strand can be installed by drilling a hole, called "a third hole", through all four cortices of the tibia and the fibula, wherein the hole through the fibula should be aligned with the hole in the elongate body of the bone fixation plate, which is used to fix the third flexible strand. In an embodiment, a K-wire is first guided through the fibula and tibia, and then a hole is drilled along the K-wire. The hole can be in the transmalleolar plane which is about 30° anterior to the coronal plane using a 3.5 mm drill bit. A needle and pull-through flexible strands are passed along the drill hole and out the intact medial skin until the first button exits the tibia on the medial surface. Then the first button is turned using the pull-through sutures. Afterwards, the first button is pulled back by pulling on the second button and the free ends of the second button. By pulling back the second button, the first button is tightened on the medial surface of the tibia.

In a next step, by pulling on the free ends of the second button, the second button is tightened on the bone fixation plate on the fibula and then by pulling further on the free ends of the second button, the fibula is pulled next to the tibia such that the syndesmosis is reduced.

In a next step, the construct is secured with three half-hitches. The flexible strand ends are cut at least 2 cm long to allow the knot and flexible strand to lie down, reducing knot prominence. Then the pull-through flexible strands are cut and removed.

In an embodiment, a knotless suture or construct thereof is utilized.

Then the first and second flexible strands are installed. To this end, two holes, called "a first hole" and "a second hole", are drilled through the tibia. The first hole in the tibia extends from an anterior position on the lateral surface of the tibia to a position (e.g., anterior) on the medial surface of the tibia. The second hole in the tibia extends from a posterior position on the lateral surface of the tibia to a position (e.g., posterior) on the medial surface of the tibia. In an embodiment, the level of the first and second holes is the same. In an embodiment, the level of the first and second holes is offset. In another embodiment, the level is at the level of the tibiofibular joint. Then the first flexible strand is threaded through the first hole, and the second flexible strand is threaded through the second hole.

The first flexible strand can be fixed at the first wing using a button. The second flexible strand can be fixed at the second wing using a button.

In an embodiment, the first and second flexible strands are fixed at the bones using buttons.

BRIEF DESCRIPTION OF THE DRAWINGS

In the following, the disclosure will be described by way of example, without limitation of the general inventive concept, on examples of embodiments and with reference to the drawings.

While the disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form disclosed, but on the contrary, the intention is to cover all modifications, equivalents and alternatives falling within the spirit and scope of the present disclosure as defined by the appended claims.

DETAILED DESCRIPTION

Figure 1:
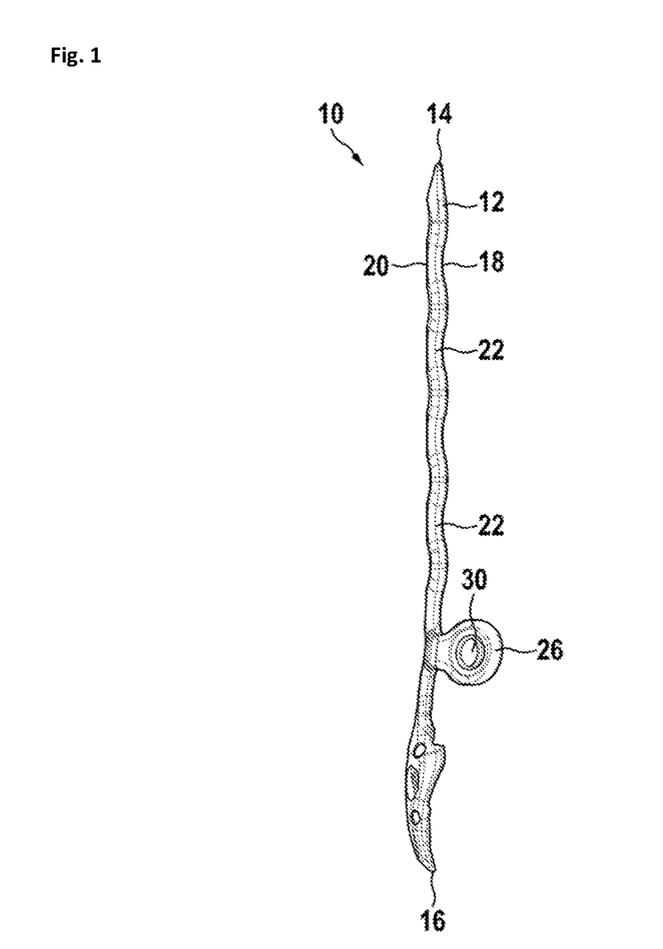
FIGS. 1, 2 and 3 show side, top, and perspective views of a bone fixation plate, respectively.
Figure 2:
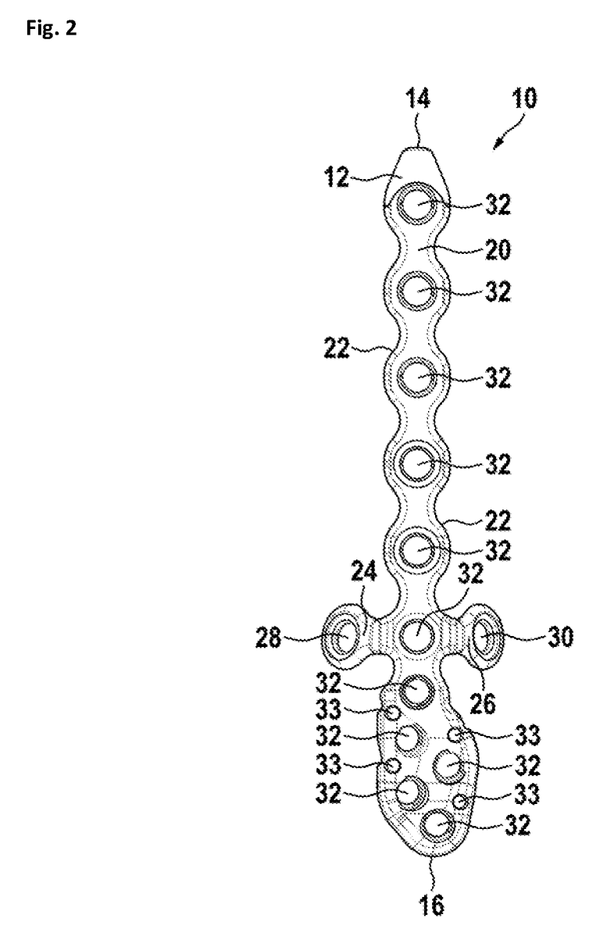
Figure 3:
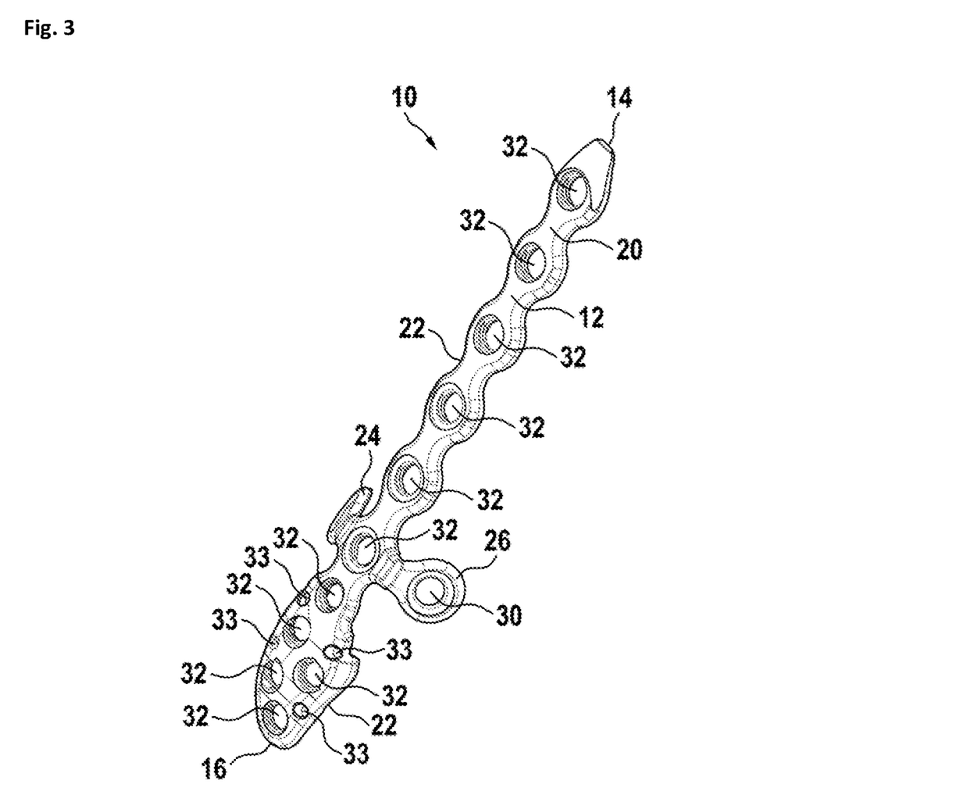

FIGS. 1, 2 and 3 show side, top and perspective views of a bone fixation plate 10.

The bone fixation plate 10 includes an elongate body 12 which has a proximal end 14, a distal end 16, an inner surface 18 (as seen in FIG. 1), and an outer surface 20. The bone fixation plate 10, in particular the elongate body 12, is adapted to be arranged on the outer surface of the distal fibula 50.

Figure 6:
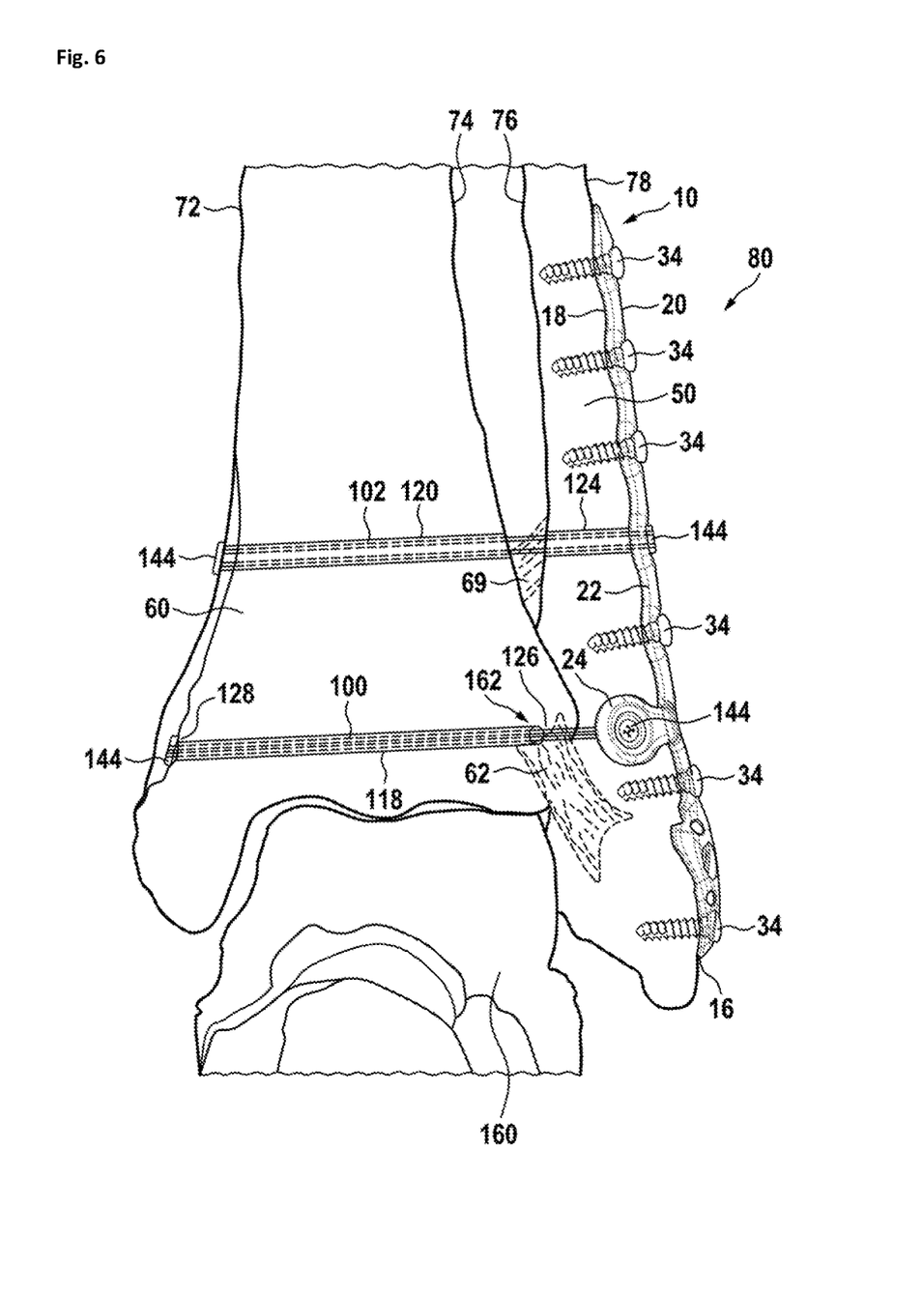
FIGS. 6 and 7 show anterior and lateral views, respectively, of a device for distal tibiofibular syndesmosis fixation when fixed to the distal tibiofibular syndesmosis of a left human foot.
Figure 7:
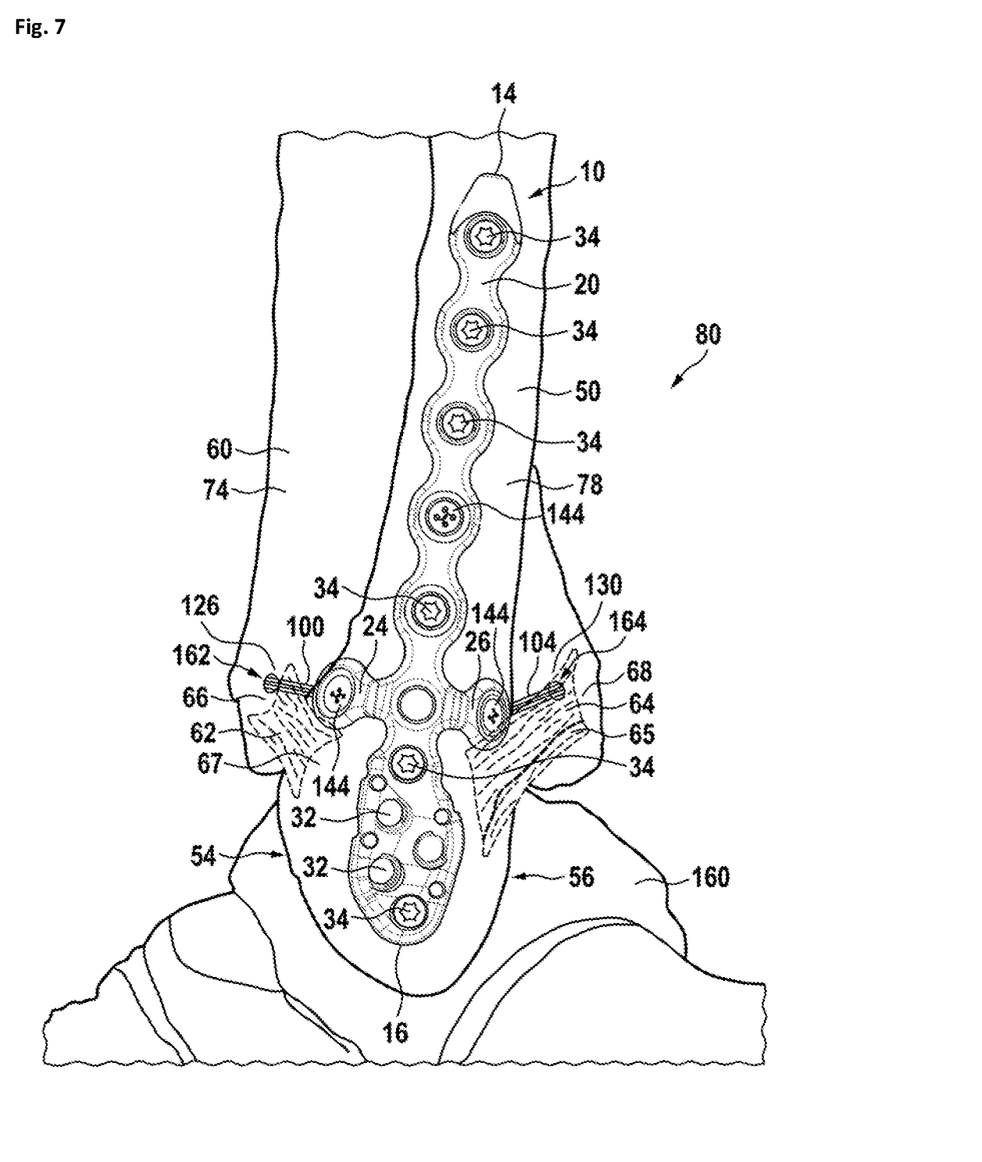

The elongate body 12 includes in this embodiment eleven holes 32 in which screws 34 (as seen in FIGS. 6 and 7) and/or a third flexible strand 102 (as seen in FIGS. 6 to 9) may be fixed. The screws 34 may be locking or non-locking. The screws 34 may be used to fix the elongate body 12 of the bone fixation plate 10 to the distal fibula 50, which might be fractured.

The elongate body 12 has lateral edges 22 arranged between the inner surface 18 and the outer surface 20.

Figure 8:
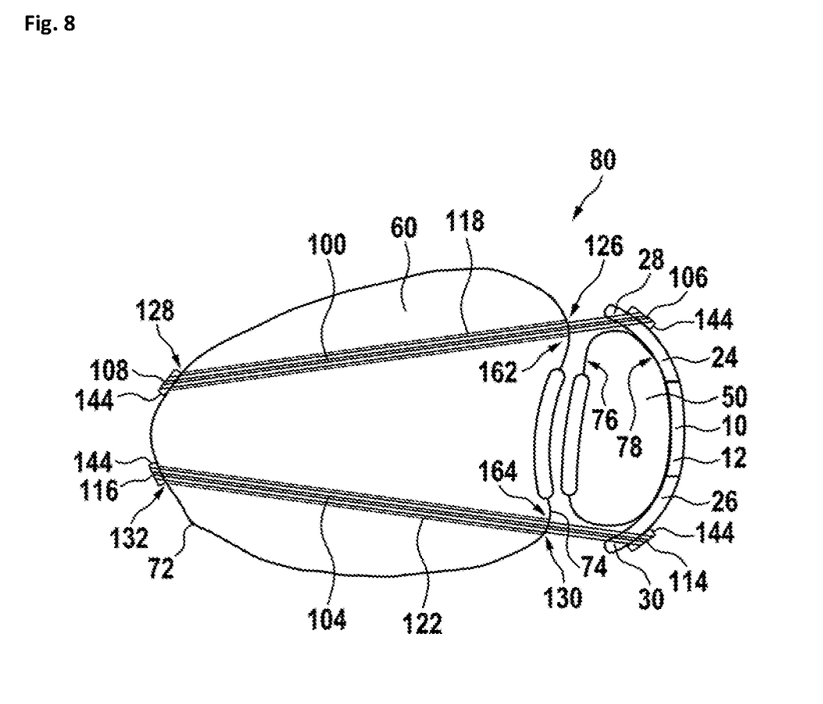
FIG. 8 shows a sectional view of the embodiment of FIGS. 6 and 7, wherein the section is at the level of the first and second flexible strands.

The bone fixation plate 10 further includes a first wing 24 and a second wing 26, which extend from the lateral edges 22 of the elongate body 12. The first wing 24 is adapted to extend from the lateral surface 78 of the distal fibula 50 towards the anterior surface 54 of the distal fibula 50 and the second wing 26 is adapted to extend from the lateral surface 78 of the distal fibula 50 towards the posterior surface 56 of the fibula 50 (as seen in FIGS. 7 and 8).

The wings 24, 26 are adapted to not directly contact the distal tibia 60 at the anterior and posterior ends 54, 56 of the fibula 50.

The first wing 24 includes a first hole 28 at which a first flexible strand 100 may be fixed and the second wing 26 includes a second hole 30 at which a second flexible strand 104 may be fixed. In one non-limiting embodiment, the first flexible strand 100 and the second flexible strand 104 are unconnected to one another.

The two wings 24, 26 are arranged symmetrically around the elongate body 12. The two wings 24, 26 may be arranged symmetrically with respect to a plane through the longitudinal axis of the elongate body 12 which is orthogonal to the outer surface 20 of the elongate body 12.

The part of the elongate body 12 that is between the proximal end 14 and the seventh hole 32 when counted from the proximal end 14 may be symmetrical with respect to the longitudinal axis of the elongate body 12. The lower part of the elongate body 12 is adapted to fit on the lower end of the distal fibula 50, and is therefore not symmetrical with respect to the longitudinal axis of the elongate body 12.

The wings 24, 26 are arranged at a distance of approximately a third of the total length of the elongate body 12 from the distal end 16 of the elongate body 12. However, the length of the elongate body 12 and the position of the wings 24, 26 may be adjusted according to the fracture inside the fibula 50. The position of the wings 24, 26 should be in the vicinity of the first and second bone orifices 162, 164. The first bone orifice 162 is located on the lateral surface 74 of the tibia 60 at the position where the first hole 118 leaves the tibia 60. The second bone orifice 164 is located on the lateral surface 74 of the tibia 60 at the position where the third hole 122 leaves the tibia 60. The first and second bone orifices 162, 164 can be seen in FIGS. 6 to 9.

Next to the distal end 16 of the elongate body 12 of the bone fixation plate 10 are small holes 33, which are much smaller than the holes 32. These small holes 33 may be used for K-wires or flexible strands. The bone fixation plate 10 may first be fixed with its distal end 16 to the distal fibula 50 using K-wires and after wards with its proximal end 14 to the distal fibula 50 using screws 34 in the holes 32.

Figure 4:
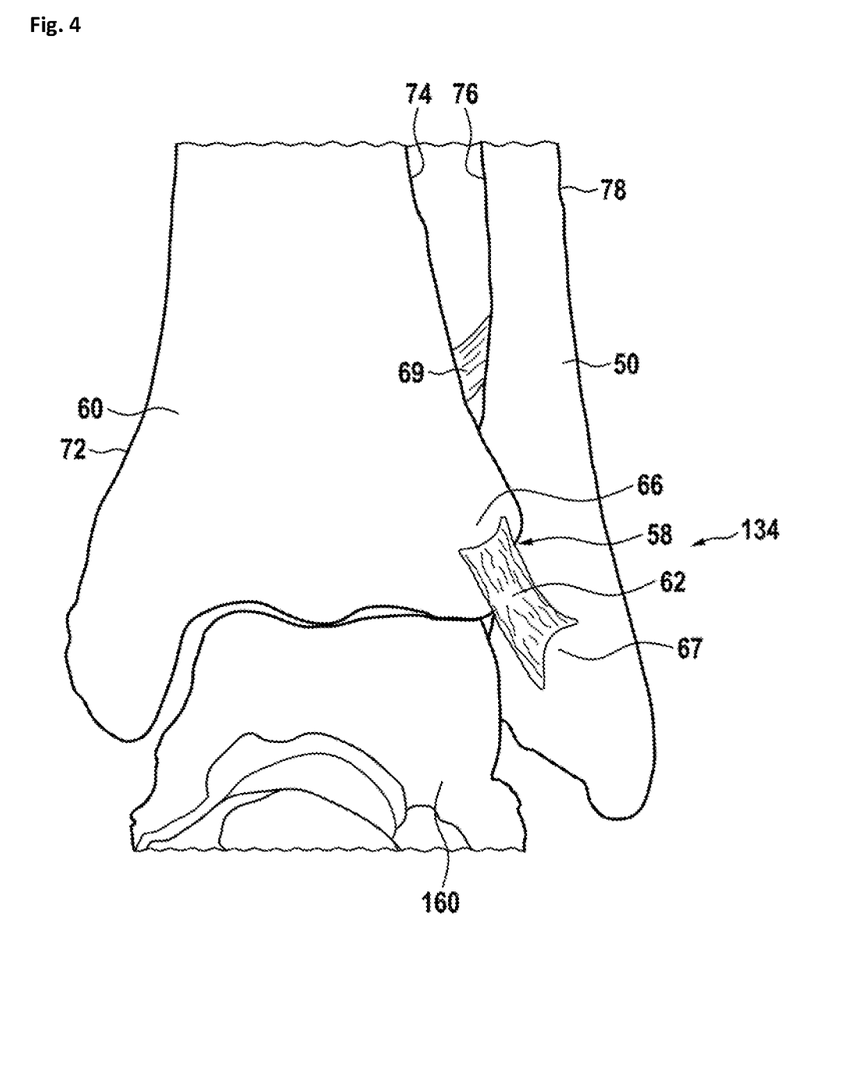
FIGS. 4 and 5 show anterior and lateral views, respectively, of the distal tibiofibular syndesmosis of a left human foot.

FIG. 4 shows an anterior view of the anatomy of a distal tibiofibular syndesmosis of a left human foot. The distal tibiofibular syndesmosis is formed by two bones and four ligaments. The two bones forming the osseous part of the syndesmosis are the distal tibia 60 on the medial and the fibula 50 on the lateral side. The ankle joint is formed by the connection of three bones. The top of the talus 160 fits inside a socket that is formed by the lower end of the distal tibia 60 and the distal fibula 50. The bottom of the talus 160 sits on the calcaneus.

The two bones are linked by the four ligaments of the distal tibiofibular syndesmosis, which are the anterior inferior tibiofibular ligament (AITFL), the posterior inferior tibiofibular ligament (PITFL), the transverse ligament (TL), and the inter-osseous ligament (IL). The anterior view of the distal tibiofibular syndesmosis shows only two of these four ligaments, i.e. the anterior inferior tibiofibular ligament (AITFL) 62, and the interosseous ligament (IL) 69.

The anterior inferior tibiofibular ligament (AITFL) 62 runs from the anterolateral tibia at Chaput's tubercle 66 laterally and inferiorly to the anterior lateral malleolus at Wagstaffe's tubercle 67.

The interosseous ligament (IL) 69 is the distal continuation of the interosseous membrane forming a strong ligament that unites the distal tibia 60 and the distal fibula 50.

Figure 5:
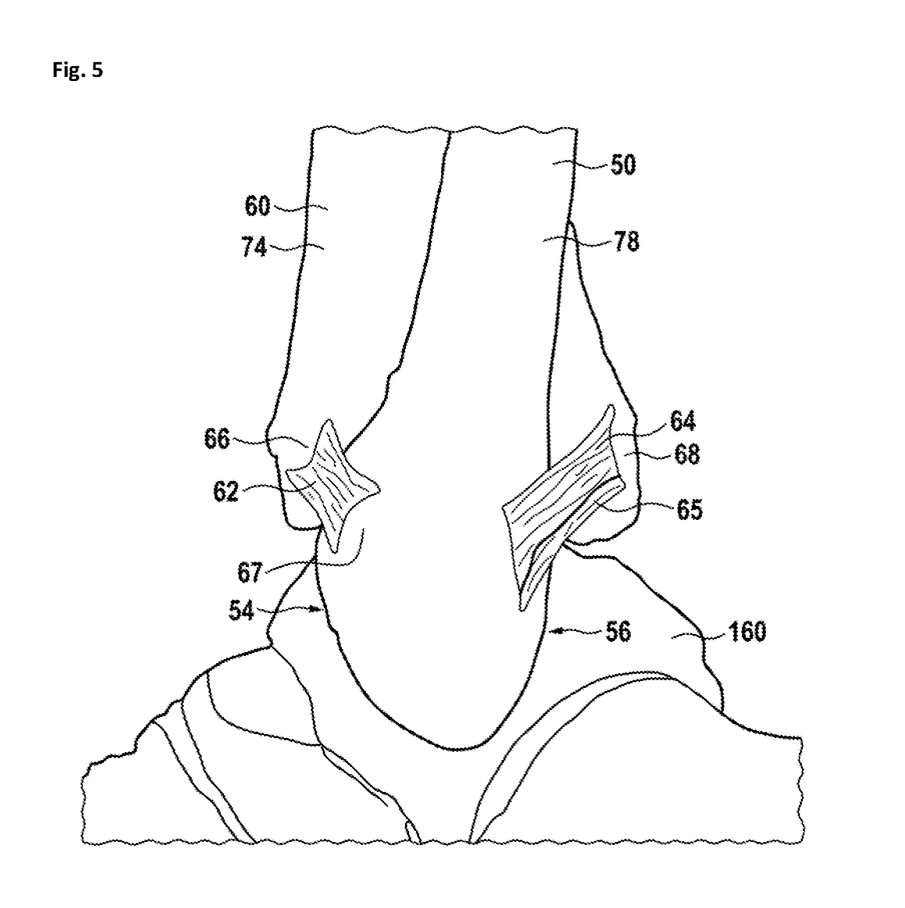

FIG. 5 shows a lateral view of the distal tibiofibular syndesmosis of a left human foot.

The lateral view of the distal tibiofibular syndesmosis shows three of the four above mentioned ligaments, i.e. the anterior inferior tibiofibular ligament (AITFL) 62, the posterior inferior tibiofibular ligament (PITFL) 64, and the transverse ligament (TL) 65. The distal fibula 50 with its lateral surface 78 is seen in front of the lateral surface 74 of the distal tibia 60.

The posterior inferior tibiofibular ligament (PITFL) 64 courses from Volkmann's tubercle 68 on the tibia 60 to the posterior lateral malleolus of the distal fibula 50. The transverse ligament 65, also known as inferior transverse ligament, is located just inferior and deep to the posterior inferior tibiofibular ligament (PITFL) 64, extending from the posterior lateral malleolus to the posterior tibia and posterior surface of the medial malleolus.

FIGS. 6 and 7 show a device 80 for distal tibiofibular syndesmosis fixation. The device 80 is fixed to the distal tibiofibular syndesmosis of a left human foot. FIG. 6 shows an anterior view, and FIG. 7 shows a lateral view.

As the ligaments 62, 64, 65, 69 may be ruptured, they are drawn with dashed lines in FIGS. 6 and 7.

The device 80 for distal tibiofibular syndesmosis fixation includes a bone fixation plate 10 similar to the one of FIGS. 1 to 3.

The bone fixation plate 10 has an elongate body 12 which has a proximal end 14, a distal end 16, an inner surface 18 and an outer surface 20. The bone fixation plate 10 further includes a first wing 24 and a second wing 26 which are adapted to be arranged on the lateral surface 78 of the fibula 50. The two wings 24, 26 are arranged symmetrically with respect to the elongate body 12.

The bone fixation plate 10 is fixed to the fibula 50 using screws 34 in holes 32 in the elongate body 12 of the bone fixation plate 10.

The ruptured ligaments of the distal tibiofibular syndesmosis are repaired using three flexible strands 100, 102, 104 which are fixed at the bone fixation plate 10 and the medial surface 72 of the tibia 60. These three flexible strands are the first flexible strand 100, the second flexible strand 104, and the third flexible strand 102, which are unconnected to one another. FIG. 6 shows the first flexible strand 100 and the third flexible strand 102. FIG. 7 shows the first flexible strand 100 and the second flexible strand 104.

For repairing the anterior and posterior tibiofibular ligaments 62, 64, the first and second flexible strands 100, 104 are used. The first flexible strand 100 is fixed with its first end 106 at the first hole 28 of the first wing 24 of the bone fixation plate 10 using a button 144 on the outer surface 20 of the first wing 24 of the bone fixation plate 10. The second flexible strand 104 is fixed with its first end 114 at the second hole 30 of the second wing 26 of the bone fixation plate 10 using a button 144 on the outer surface 20 of the second wing 26 of the bone fixation plate 10. FIG. 7 only shows the part of the first and second flexible strands 100, 104 between the wings 24, 26 and the first hole 118 and the third hole 122 of the tibia 60. FIG. 7 shows only the first and second flexible strand 100, 104, while the third flexible strand 102 is not displayed.

The first flexible strand 100 runs from the button 144 of the first wing 24 to the first anterior position 126 on the lateral surface 74 of the tibia 60, where it enters the first hole 118 in the tibia 60 through the first bone orifice 162, to the first position 128 (e.g., anterior) on the medial surface 72 of the tibia 60, where it is fixed using a button 144. This can also be seen in FIG. 8. As each of the flexible strands 100, 102, 104 of this embodiment is a suture-button construct, each suture is drawn with four lines corresponding to the four fibers or threads of the suture.

The second flexible strand 104 runs from the button 144 of the second 26 wing to the second posterior position 130 on the lateral surface 74 of the tibia 60, where it enters the third hole 122 in the tibia 60 through the second bone orifice 164, to the second position 132 (e.g., posterior) on the medial surface 72 of the tibia 60, where it is fixed using a button 144. This can also be seen in FIG. 8.

For repairing the interosseous ligament 69, the third flexible strand 102 is fixed with its first end 110 at a hole 32 in the elongate body 12 of the bone fixation plate 10 using a button 144 on the outer surface 20 of the elongate body 12 of the bone fixation plate 10. The third flexible strand 102 runs through the second hole 120 in the tibia 60 and the hole 124 in the fibula and is fixed with its second end 112 at the medial surface 72 of the tibia 60 using a button 144. This can also be seen in FIG. 9. The button 144 which rests on the medial surface 72 of the tibia 60 can for example be pulled through the second hole 120 of tibia 60 from the lateral surface 74 of tibia 60 and flipped to rest on the medial surface 72 of the tibia 60. This may be done without pulling the button 144 through the fibula 50.

A modification of the bone fixation plate 10 can have wings 24, 26 moved further distally to approximate to the anatomical insertion point of the ligaments in fibula.

Figure 9:
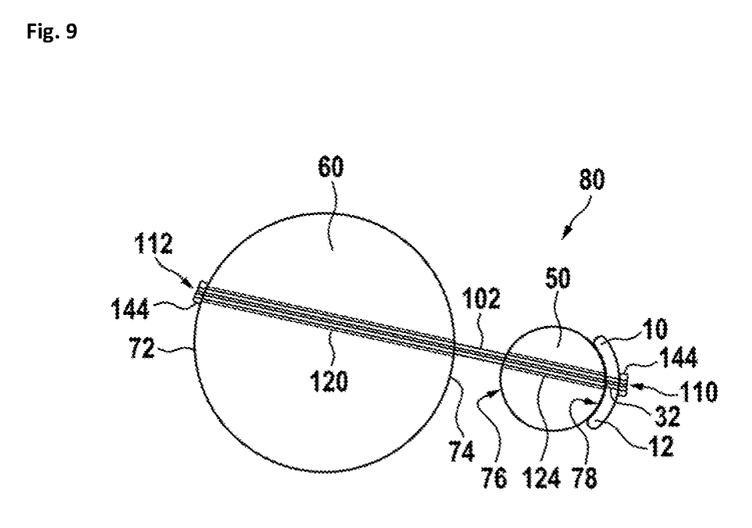
FIG. 9 shows a sectional view of the embodiment of FIGS. 6 and 7, wherein the section is at the level of the third flexible strand.

FIGS. 8 and 9 show sectional views at different levels of the embodiment of FIGS. 6 and 7. In FIG. 8 the sectional view is at the level of the first and second flexible strands 100, 104. In FIG. 9 the sectional view is at the level of the third flexible strand 102. Both FIG. 8 and FIG. 9 are inferior views.

FIG. 8 shows an inferior, sectional view at the level of the first and second flexible strands 100, 104. This section is at the height of the tibiofibular joint 134.

FIG. 8 shows the tibia 60 on the left and the fibula 50 on the right. The bone fixation plate 10 is arranged on top of the lateral surface 78 of the fibula 50. The elongate body 12 of the bone fixation plate 10 is arranged on the center of the lateral surface 78 of the fibula 50. The first wing 24 of the bone fixation plate 10 extends from the elongate body 12 of the bone fixation plate 10 towards the anterior surface 54 of the distal fibula 50, near where the first hole 28 of the first wing 24 is arranged. The first hole 28 of the first wing 24 does not fully contact the distal fibula 50. The second wing 26 of the bone fixation plate 10 extends from the elongate body 12 of the bone fixation plate 10 towards the posterior surface 56 of the distal fibula 50, near where the second hole 30 of the second wing 26 is arranged. The second hole 30 of the second wing 26 does not fully contact the distal fibula 50.

The first flexible strand 100 which is fixed at a button 144 at the outer surface 20 of the first wing 24 of the bone fixation plate 10 runs through the first hole 28 towards the lateral surface 74 of the tibia 60, where it enters at the first anterior position 126 the first hole 118 in tibia 60 through the first bone orifice 162. The first flexible strand 100 does not run through the fibula 50, instead it passes sideward at the fibula. The first flexible strand 100 then continues to go through the first hole 118 and is fixed with another button 144 on the medial surface 72 of the tibia 60. This button 144 is larger than the orifice, wherein the first hole 118 leaves the medial surface 72 of the tibia 60 at the first position 128 (e.g., anterior) on the medial surface 72 of the tibia 60. This button 144 rests on the outside of the bone on the medial surface 72 of tibia 60.

The second flexible strand 104 which is fixed at a button 144 at the outer surface 20 of the second wing 24 of the bone fixation plate 10 runs through the second hole 30 towards the lateral surface 74 of the tibia 60, where it enters at the second posterior position 130 the third hole 122 in tibia 60 through the second bone orifice 164. The second flexible strand 104 does not run through the fibula 50 instead it passes sideward at the fibula. The second flexible strand 104 then continues to go through the third hole 122 and is fixed with another button 144 on the medial surface 72 of the tibia 60. This button 144 is larger than the orifice, wherein the third hole 122 leaves the medial surface 72 of the tibia 60 at the second position 132 (e.g., posterior) on the medial surface 72 of the tibia 60. This button 144 rests on the outside of the bone on the medial surface 72 of tibia 60.

FIG. 9 shows an inferior, sectional view at the level of the third flexible strand 102. This section is at a height slightly above the upper end of the distal tibiofibular joint articular cartilage. FIG. 9 shows the tibia 60 on the left and the fibula 50 on the right. The bone fixation plate 10 is arranged on top of the lateral surface 78 of the fibula 50. The elongate body 12 of the bone fixation plate 10 is arranged on the center of the lateral surface 78 of the fibula 50.

The third flexible strand 102 which is fixed at a button 144 at the outer surface 20 of the elongate body 12 of the bone fixation plate 10, runs through a hole 32 in the elongate body 12 of the bone fixation plate 10, then enters the hole 124 in the fibula 50, exits the fibula 50, runs between the medial surface 76 of the fibula and the lateral surface 74 of the tibia, then enters the second hole 120 in the tibia 60 and is fixed with yet another button 144 on the medial surface 72 of the tibia 60. This button 144 is larger than the orifice, wherein the second hole 120 leaves the medial surface 72 of the tibia 60 on the medial surface 72 of the tibia 60.

It will be appreciated to those skilled in the art having the benefit of this disclosure that this disclosure is believed to provide a bone fixation plate and a device for distal tibiofibular syndesmosis fixation. Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the disclosure. It is to be understood that the forms of the disclosure shown and described herein are to be taken as the presently preferred embodiments. Elements and materials may be substituted for those illustrated and described herein, parts and processes may be reversed, and certain features of the disclosure may be utilized independently, all as would be apparent to one skilled in the art after having the benefit of this description of the disclosure. Changes may be made in the elements described herein without departing from the spirit and scope of the disclosure as described in the following claims.

What is claimed is:

1. A device for syndesmosis fixation, comprising:
   a bone fixation plate including an elongated body including a proximal end, a distal end, an inner surface adapted to be arranged on an outer surface of a distal fibula, an outer surface, a first lateral edge and a second lateral edge arranged between said inner surface and said outer surface, a first wing extending at an angle from said first lateral edge at a location between said proximal end and said distal end, a second wing extending at said angle from said second lateral edge at a location between said proximal end and said distal end, and a third hole extending through said elongated body;
   a first flexible strand-button construct fixated within a first hole of said first wing;
   a second flexible strand-button construct fixated within a second hole of said second wing; and
   a screw or a third flexible strand-button construct fixated within said third hole.

2. The device as recited in claim 1, wherein said angle is between 20° and 70° with respect to a longitudinal plane of the elongated body.

3. The device as recited in claim 1, wherein said first, second, and third flexible strand-button constructs each include a flexible strand connected between a first button and a second button.

4. The device as recited in claim 3, wherein the flexible strand is a tape.

5. The device as recited in claim 1, wherein said first wing extends toward an anterior surface of a distal fibula and said second wing extends toward a posterior surface of said distal fibula when said bone fixation plate is positioned against said distal fibula.

6. The device as recited in claim 1, wherein said first wing is arranged at approximately a same height as an anterior tibiofibular ligament and said second wing is arranged at approximately a same height as a posterior tibiofibular ligament when said bone fixation plate is positioned against a distal fibula.

7. The device as recited in claim 1, wherein said elongated body includes a first part between said proximal end and said first and second wings and a second part between said distal end and said first and second wings, and said first part is symmetrical about a longitudinal axis of said elongated body and said second part is non-symmetrical about said longitudinal axis.

8. The device as recited in claim 7, wherein said second part includes a plurality of holes, and at least two holes of said plurality of holes include different sizes.

9. The device as recited in claim 8, wherein the plurality of holes of the second part consists of five holes and four smaller holes.

10. The device as recited in claim 7, wherein the first part includes a plurality of holes, and the plurality of holes of the first part consists of five holes.

11. The device as recited in claim 7, wherein the second part includes an enlarged width relative to the first part, and wherein the first wing and the second wing are located proximally of a location when the second part begins to increase in width.

12. The device as recited in claim 1, wherein said first wing and said second wing are arranged at a distance of approximately one third of a total length of said elongated body as measured from said distal end.

13. The device as recited in claim 1, wherein at least one of said first wing and said second wing is bendable relative to said elongated body.

14. The device as recited in claim 1, wherein at least a portion of the first wing and the second wing is orthogonal to a longitudinal axis of the elongated body.

15. A method of syndesmosis fixation, comprising:
   positioning the bone fixation plate of claim 1 against the distal fibula such that the elongated body of the bone fixation plate extends along a lateral surface of the distal fibula, the first wing extends toward an anterior surface of the distal fibula, and the second wing extends toward a posterior surface of the distal fibula; and
   fixating the first flexible strand-button construct within the first hole of the first wing, wherein the first flexible strand-button construct includes a first button received within the first hole, a second button received against a medial surface of a tibia, and a flexible strand extending between the first button and the second button.

16. The method as recited in claim 15, wherein the flexible strand extends through the first hole toward a lateral surface of the tibia, then through a passage in the tibia extending from the lateral surface of the tibia to the medial surface of the tibia.

17. The method as recited in claim 15, wherein the first flexible strand-button construct repairs an anterior tibiofibular ligament.

18. The method as recited in claim 15, comprising, either prior to or after fixating the first flexible strand-button construct:
   fixating the second flexible strand-button construct within the second hole of the second wing, wherein the second flexible strand-button construct includes a third button received within the second hole, a fourth button received against the medial surface of the tibia, and a second flexible strand extending between the third button and the fourth button.

19. The method as recited in claim 18, comprising, either prior to, between, or after fixating the first flexible strand-button construct and the second flexible strand-button construct:

fixating the third flexible strand-button construct within the third hole of the elongated body, wherein the third flexible strand-button construct includes a fifth button received within the third hole, a sixth button received against the medial surface of the tibia, and a third flexible strand extending between the fifth button and sixth button.

* * * * *